(12) United States Patent
Gee

(10) Patent No.: US 12,734,068 B2
(45) **Date of Patent: *Sep. 15, 2026**

(54) SURGICAL HANDPIECE FOR PROVIDING TRANSVERSE AND LONGITUDINAL MOTION TO A SURGICAL TIP

(71) Applicant: Johnson & Johnson Surgical Vision, Inc., Santa Ana, CA (US)

(72) Inventor: Jacob Gee, Blanchester, OH (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 887 days.

This patent is subject to a terminal disclaimer.

(21) Appl. No.: 17/595,310

(22) PCT Filed: May 15, 2020

(86) PCT No.: PCT/IB2020/054647

§ 371 (c)(1),
(2) Date: Nov. 12, 2021

(87) PCT Pub. No.: WO2020/234731

PCT Pub. Date: Nov. 26, 2020

(65) Prior Publication Data

US 2022/0192880 A1 Jun. 23, 2022

Related U.S. Application Data

(60) Provisional application No. 62/849,780, filed on May 17, 2019.

(51) Int. Cl.

*A61F 9/007* (2006.01)
*B06B 1/02* (2006.01)
(Continued)

(52) U.S. Cl.

CPC ........ *A61F 9/00745* (2013.01); *B06B 1/0284* (2013.01); *B06B 1/0614* (2013.01);
(Continued)

(58) Field of Classification Search

CPC . A61F 9/00745; B06B 1/0284; B06B 1/0614; B06B 2201/76; A61B 2017/320098
See application file for complete search history.

(56) References Cited

U.S. PATENT DOCUMENTS

| | | | |
|---|---|---|---|
| 2,838,695 | A | 6/1958 | Thurston |
| 2,838,696 | A | 6/1958 | Thurston |

(Continued)

FOREIGN PATENT DOCUMENTS

| | | | |
|---|---|---|---|
| EP | 0910292 | B1 | 7/2005 |
| JP | H0329645 | A | 2/1991 |

(Continued)

OTHER PUBLICATIONS

U.S. Appl. No. 17/231,450, titled, “Compensating for Imperfect Behavior of Multi-Piezoelectric Crystal,” filed Apr. 15, 2021.

(Continued)

*Primary Examiner* — Kathleen S Holwerda
*Assistant Examiner* — James R Mcginnity

(57) ABSTRACT

An apparatus, system and method for providing a surgical handpiece. The apparatus, system and method may include: an ultrasonic horn having an emulsifying needle at a distal end thereof; a plurality of piezoelements about a proximal end of the ultrasonic horn; a plurality of flexible electrode segments comprising first sets of the electrode segments atop each of the piezoelements and second sets of the electrode segments below each of the piezoelements, and comprising at least pairs of the electrode segments in which each pair comprises an electrode segment atop a one of the piezoelements and a paired electrode segment below that (Continued)

one of the piezoelements; a plurality of flexible interconnections that electrically interconnect at least the first sets and second sets, and the pairs, flexibly about each of the plurality of piezoelements; and a power source applied via a controlled double-pole, double-throw (DPDT) switch.

17 Claims, 11 Drawing Sheets

(51) Int. Cl.
*B06B 1/06* (2006.01)
*A61B 17/32* (2006.01)

(52) U.S. Cl.
CPC ............. *A61B 2017/320098* (2017.08); *B06B 2201/76* (2013.01)

(56) References Cited

U.S. PATENT DOCUMENTS 2,838,699 A 6/1958 Mock
4,872,346 A * 10/1989 Kelly-Fry ............ A61B 8/0825 73/627
4,961,424 A * 10/1990 Kubota ..................... B06B 3/02 601/2
5,162,044 A 11/1992 Gahn et al.
5,814,922 A * 9/1998 Uchino .................. H10N 30/40 310/366
6,274,963 B1 8/2001 Estabrook et al.
6,346,764 B1 * 2/2002 Boyd ..................... H10N 30/40 310/366
6,352,519 B1 3/2002 Anis et al.
7,794,414 B2 9/2010 Rabiner et al.
8,303,613 B2 * 11/2012 Crandall ............... B06B 1/0611 606/171
9,216,035 B2 12/2015 Urich et al.
9,517,346 B2 12/2016 Lee et al.
2004/0242709 A1 12/2004 Oguro et al.
2004/0267298 A1 * 12/2004 Cimino .......... A61B 17/320068 606/167
2005/0187513 A1 8/2005 Rabiner et al.
2007/0249941 A1 10/2007 Salehi et al.
2008/0258563 A1 10/2008 Hodges
2009/0005712 A1 1/2009 Raney
2009/0099536 A1 4/2009 Akahoshi
2009/0149801 A1 6/2009 Crandall et al.
2012/0143233 A1 6/2012 Sinelnikov
2013/0006266 A1 1/2013 Crandall et al.
2013/0253559 A1 9/2013 Slipszenko et al.
2014/0055932 A1 2/2014 Nakamura
2014/0217832 A1 8/2014 Phadke
2015/0173950 A1 6/2015 Nallakrishnan
2015/0257778 A1 9/2015 Harrington et al.
2016/0038340 A1 2/2016 Raney
2018/0078268 A1 3/2018 Messerly et al.
2019/0008680 A1 1/2019 Jochinsen et al.
2020/0268398 A1 * 8/2020 Gill ................ A61B 17/320068
2020/0384502 A1 * 12/2020 Downey ............... B06B 1/0253
2021/0330493 A1 10/2021 Steen et al.
2021/0353461 A1 11/2021 Govari et al.
2021/0361481 A1 11/2021 Gliner et al.
2022/0105688 A1 * 4/2022 Dippel ................... B33Y 70/10
2022/0192881 A1 * 6/2022 Gee ........................... G01T 1/00
2022/0331159 A1 10/2022 Gliner
2023/0240889 A1 8/2023 Fuchs et al.
2023/0338189 A1 10/2023 Fuchs

FOREIGN PATENT DOCUMENTS

JP H11206162 A 7/1999
WO 2010018760 A1 2/2010
WO 2010057059 A1 5/2010
WO 2015126914 A1 8/2015
WO 2022219464 A1 10/2022
WO 2023017333 A1 2/2023

OTHER PUBLICATIONS

U.S. Appl. No. 17/590,184, titled, "Equalizing Multi-Channel Driving Signals of Segmented Piezoelectric Crystals," filed Feb. 1, 2022.
Co-pending U.S. Appl. No. 17/231,450, filed Apr. 15, 2021, 20 pages.
Chen Y., et al., "Tip Trajectories of a Smart Micro-cantilever Beam: Analysis and Design," Smart Materials and Structures, 2009, vol. 18 (11), pp. 115012 (10 pages), XP020168951.

* cited by examiner 16
14
12
16
14
20
20
10
10
15
17
17
10a
A

A
12

402
106
910
114
700, 800
A

SURGICAL HANDPIECE FOR PROVIDING TRANSVERSE AND LONGITUDINAL MOTION TO A SURGICAL TIP

CROSS-REFERENCE TO RELATED APPLICATIONS

This application is a U.S. national stage of and claims the benefit under 35 U.S.C. § 371 of International Patent Application No. PCT/IB2020/054647, filed May 15, 2020, which claims priority to U.S. Provisional Patent Application No. 62/849,780, filed on May 17, 2019, the entire contents of which are hereby incorporated by reference in their entirety.

BACKGROUND

Field of the Disclosure

The present invention relates to phacoemulsification and similar procedures of the eye, and, more particularly, to inducing both transverse and longitudinal motion in a surgical emulsifying tip.

Description of the Background

A cataract is an opacity that develops in the lens of an eye. Cataracts are the most significant cause of blindness worldwide.

Phacoemulsification is a medically recognized technique utilized for crystalline lens removal, which is a highly prevalent method of treating cataracts. Phacoemulsification includes making a corneal and/or scleral incision, and the insertion of a portion of a phacoemulsification handpiece, which is typically comprised of a vibrating needle that is ultrasonically driven in order to emulsify, i.e., to liquefy, the natural crystalline lens and/or an unhealthy aspect, such as a cataract, associated therewith. Once removed, the emulsified lens may be replaced with a prosthetic intraocular lens implant.

The phacoemulsification handpiece is generally coupled to an irrigation source and an aspiration pump. As referenced, the handpiece includes a distal tip for insertion within the anterior chamber of the patient's eye and which uses ultrasonic energy to emulsify the crystalline lens. The handpiece further includes at least one irrigation port proximal to the distal tip, which is coupled to the irrigation source, such as a balanced salt solution, via an irrigation line; and an aspiration port at the distal tip, which is coupled to one or more aspiration pumps via an aspiration line. Fluid from the irrigation source, which may be an elevated bottle of saline solution and/or a pressurized irrigation source, is directed into the eye via the irrigation line and the irrigation port, and the irrigation fluid and emulsified crystalline lens material are aspirated from the eye by the one or more aspiration pumps via the aspiration port and the aspiration line.

In a phacoemulsification handpiece, a horn coupled with a hollow needle is generally used. The horn resides in a housing which typically includes an irrigation port for introducing the aforementioned irrigation fluid through the handpiece and into the affected eye.

A series of ultrasonic elements, e.g. piezoelectric crystals, referred to herein as a "stack", is disposed about the horn. When the stack is ultrasonically oscillated, the ultrasonic elements expand and contract, thereby causing rapid longitudinal vibration in the horn, and thus in the needle attached to the horn. The vibration emulsifies the cataractous lens.

However, during phacoemulsification in particular, it is possible for the aspirating phacoemulsification handpiece to become occluded by emulsified particulate that blocks the tip of the needle of the aspirating handpiece. For volumetric flow pumps, this blockage can result in increased vacuum. For a vacuum-based pump, this blockage can result in a volumetric fluid flow drop off near the aspiration port. In each such case, once the occlusion is cleared, the resulting rush of fluid from the anterior chamber into the aspiration line can outpace the volumetric flow of new fluid into the eye from the irrigation source, which may lead to severe eye trauma. It is understood that transverse motion induced in the needle may help in clearing such obstructions to the aspiration aspects of the handpiece.

Transverse motion would provide a side-to-side or "sanding" motion that would remove cataract material without the negative effect of kicking the material away from the tip, which happens with longitudinal motion. However, with transverse motion arises the potential for cataract material to get clogged in the tip or along the lumen of the transducer and/or handpiece. In such a case, the longitudinal motion through the tip helps clear material.

Flexible electronics are electronic circuits mounted on flexible substrates. The substrates may be composed of poly(ethylene terephthalate) (PET), poly(ethylene naphthalate) (PEN), poly(imide)-foil (PI), poly carbonate (PC), thermoplastic polyurethane (TPU), paper, textile, PEEK and polyester, by way of example. Flexible electronics may be manufactured using identical components as those used for rigid printed circuit boards, but allow the flexible circuit to conform to a desired shape for its use.

Flexible printed circuits (FPC) may be created using additive or subtractive printing and photolithographic technologies. FPC may include additively manufactured, i.e., printed, electronic circuits and traces on a flexible substrate, such as the substrates discussed above. Further, such traces or circuits may be formed using etching away of conductive or nonconductive surfaces, for example, i.e., subtractive processes.

Additively printed flexible electronics use additive methods to create the electrical traces and/or other devices on the flexible substrate. Printing typically defines patterns on various substrate materials, such as using screen printing, flexography, gravure, offset lithography, and inkjet. Electrically functional electronic or optical inks may be deposited on the substrate using one or more of these printing techniques, thus creating active or passive devices and/or traces.

The printed electronics may use inorganic or organic inks. These ink materials may be deposited by solution-based, vacuum-based, or other processes. Ink layers may be applied one atop another. Printed electronic features may be or include semiconductors, metallic or non-metallic conductors, nanoparticles, nanotubes, etc.

Flex circuits may be used as connectors in various applications where flexibility, space savings, or production constraints limit the serviceability of rigid circuit boards or hand wiring. Common applications of PFCs include computer keyboards, industrial and medical devices, and cellular telephones.

Printed flex electronics provide a low-cost, high-volume volume fabrication in heretofore unknown ways, and without substantial increased costs. For example, printed electronics on flexible substrates allows electronics to be placed on or around curved surfaces, without the extraordinary expense that the use of conventional electronics in such a scenario would require.

The selection of the flex circuit printing method(s) used may be determined by requirements related to the printed layers, layer characteristics, and the properties of the printed materials. Such requirements may include the flexibility, the thicknesses, any holes or subtractive aspects of the circuit, and material types, as well as by the economic and technical considerations of a final, printed product.

Thus, a need exists to efficiently induce both longitudinal and transverse motion in a phacoemulsification needle, and to do so using a more efficient and expedient formation process for the needle using flexible printed circuits.

SUMMARY

The disclosed apparatus, system and method is and may include at least a surgical handpiece, comprising: an ultrasonic horn having an emulsifying needle at a distal end thereof; a plurality of piezoelements about a proximal end of the ultrasonic horn; a plurality of flexible electrode segments comprising first sets of the electrode segments atop each of the piezoelements and second sets of the electrode segments below each of the piezoelements, and comprising at least pairs of the electrode segments in which each pair comprises an electrode segment atop a one of the piezoelements and a paired electrode segment below that one of the piezoelements; a plurality of flexible interconnections that electrically interconnect at least the first sets and second sets, and the pairs, flexibly about each of the plurality of piezoelements; and a power source applied via a controlled double-pole, double-throw (DPDT) switch.

A first oscillating uniform excitation of the first sets with a first uniform opposing excitation of the second sets by the power source via the plurality of flexible interconnections may effectuate a longitudinal ultrasonic vibration of the ultrasonic horn. A second oscillating uniform excitation of first ones of the pairs with a second uniform opposing excitation of other ones of the pairs via the plurality of flexible interconnections may effectuate a transversal ultrasonic vibration of the ultrasonic horn.

Thus, the disclosed embodiments provide an apparatus, system, and method for efficiently inducing both longitudinal and transverse motion in a phacoemulsification needle using a more efficient and expedient formation process for the needle using flexible printed circuits.

BRIEF DESCRIPTION OF THE FIGURES

Referring now to the figures incorporated herein, shown are non-limiting embodiments of the present disclosure, wherein like numerals may, but do not necessarily, represent like elements, and wherein.

DETAILED DESCRIPTION

Figure 1:
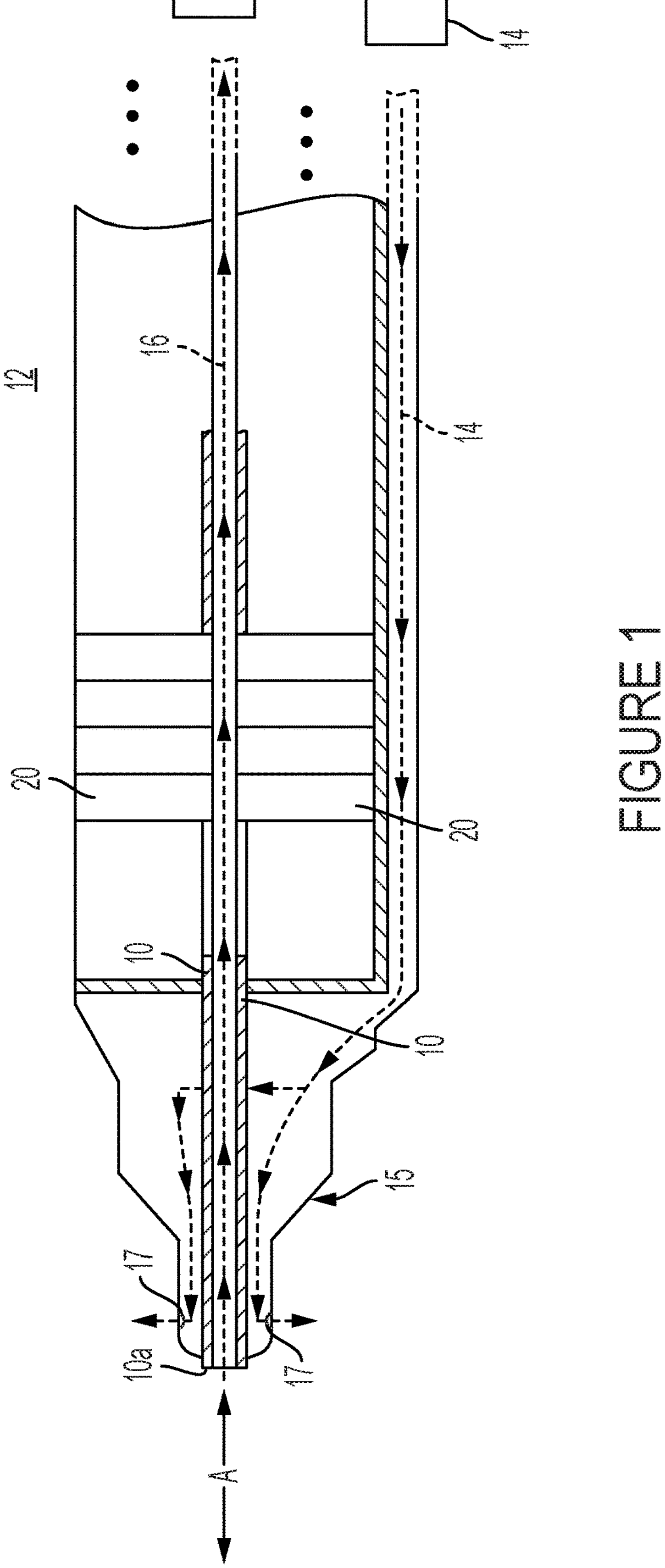
FIG. 1 is an illustration of aspects of the embodiments.

The figures and descriptions provided herein may have been simplified to illustrate aspects that are relevant for a clear understanding of the herein described apparatuses, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, for the sake of brevity a discussion of such elements and operations may not be provided herein. However, the present disclosure is deemed to nevertheless include all such elements, variations, and modifications to the described aspects that would be known to those of ordinary skill in the art.

Exemplary embodiments are provided throughout so that this disclosure is sufficiently thorough and fully conveys the scope of the disclosed embodiments to those who are skilled in the art. Numerous specific details are set forth, such as examples of specific components, devices, and methods, to provide a thorough understanding of embodiments of the present disclosure. Nevertheless, it will be apparent to those skilled in the art that certain specific disclosed details need not be employed, and that exemplary embodiments may be embodied in different forms. As such, the exemplary embodiments should not be construed to limit the scope of the disclosure. As referenced above, in some exemplary embodiments, well-known processes, well-known device structures, and well-known technologies may not be described in detail.

The terminology used herein is for the purpose of describing particular exemplary embodiments only and is not intended to be limiting. For example, as used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The steps, processes, and operations described herein are not to be construed as necessarily requiring their respective performance in the particular order discussed or illustrated, unless specifically identified as a preferred or required order of performance. It is also to be understood that additional or alternative steps may be employed, in place of or in conjunction with the disclosed aspects.

When an element or layer is referred to as being "on", "engaged to", "connected to" or "coupled to" another element or layer, it may be directly on, engaged, connected or coupled to the other element or layer, or intervening elements or layers may be present, unless clearly indicated otherwise. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). Further, as used herein the term "and/or" includes any and all combinations of one or more of the associated listed items.

Yet further, although the terms first, second, third, etc. may be used herein to describe various elements, components, regions, layers and/or sections, these elements, components, regions, layers and/or sections should not be limited by these terms. These terms may be only used to distinguish one element, component, region, layer or section from another element, component, region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the exemplary embodiments.

Certain types of ocular dysfunction, such as cataracts, are commonly treated with surgical procedures, such as to remove the natural lens from the eye and replace it with a clear artificial lens. More particularly and by way of example, phacoemulsification refers to a surgery, often employed when a patient suffers from cataracts, in which the eye's natural lens is emulsified by applying ultrasonic energy to the lens using a handpiece. As the lens is emulsified, it is aspirated from the eye by applying a vacuum to the emulsified lens material. During the procedure, irrigation fluid is administered into the eye as the emulsified material is aspirated, thereby maintaining pressure in the interior of the eye. The emulsified lens is then typically replaced with a clear artificial intraocular lens (IOL).

To perform the afore-discussed and similar procedures, a surgeon often utilizes a computer-controlled system of specialized equipment called a phacoemulsification system console to control and execute the ultrasonic emulsification and aspiration of the natural lens of the eye prior to inserting the IOL. During the procedure, information such as the amount of vacuum applied to aspirate, the flow rate, a microscopic view of the operating field, and the like, may be displayed on and controllable from a user interface of the phacoemulsification system console, or on a separate screen, computer, or other viewing device, and may be monitored and verbally reported by support staff during the procedure. At least some of this data is commonly used to inform and improve ongoing and subsequent procedures.

In phacoemulsification, the ultrasonic vibration of the handpiece tip is generally paired with irrigation and the aspiration in order to safely and effectively perform the surgery, as discussed throughout. In a typical cataract surgery, by way of example, the vacuum pulls the lens material up to the vibrating tip and holds it in place to be broken down into pieces small enough to be aspirated via the handpiece out of the eye. However, a common issue referred to as post occlusion surge may lead to severe trauma to structures of the eye during performance of the surgery. Post occlusion surge occurs when the tip of the needle is partially or completely blocked, such as by the emulsified material, and the vacuum consequently builds between the handpiece and the one or more pumps.

The embodiments provide an ultrasonic horn, such as for use in phacoemulsification surgeries, that provides longitudinal motion at the needle tip, and provides a transversal/flexural motion at the needle tip to emulsify the lens of the eye. In short, the transversal motion provides a side-to-side or back-and-forth "sanding" motion at the tip to break up the lens and the longitudinal motion that causes the occluding particulate to move away from the tip, thereby leading to the aspiration sucking the entire particle back such that the occlusion occurs anew.

The ultrasonic transducers that drive both motion types in the disclosure may each respectively include wired, semi-circular electrodes at the top and bottom of a piezo-element. The individual transducers are provided in a stack of transducers about the horn so as to ultrasonically ring the horn pursuant to control signals.

More specifically, control signals may drive at least one digital or analog double-pole, double-throw (DPDT) switching circuits. When the DPDT switch is in a first position, the opposing semi-circular electrodes receive alternating energy, which causes the respective piezoelement to grow on one side and shrink on the other side, thereby effectuating a side to side excitation generating a flexural/transversal mode. However, when the DPDT switch is in a second position, the transducers cause the horn's piezodisks to grow and shrink together, thus effectuating a longitudinal mode.

Additionally, and as discussed throughout, the formation of many small aspects of small devices may integrate the use of flexible circuitry and the processes of additive manufacturing, deposition and etching. That is, traces, such as conductive traces, dielectric traces, insulating traces, and the like, which include formation of device features such as waveguides, via, connections, and the like, may be formed on a flexible substrate additively or subtractively.

By way of non-limiting example, the ability to print electronic traces on plasticized substrates, allowing those substrates to be conformed after printing, has been developed. Thereby, for example, devices and elements of devices may be created and formed to the device into which the elements are to be integrated.

The suitability of printed electronics to be used on flexible substrates in awkwardly sized and shaped locations within a device and in relation to uneven topologies may allow for printed electronics to be integrated as part of a phacoemulsification handpiece. More particularly, flex circuits may be used to provide segmented electrodes that provide for both longitudinal and transversal motion in the emulsifying needle of a phacoemulsification handpiece.

FIG. 1 illustrates a handpiece 12 having ultrasonic horn 10. The horn 10 is fixedly associated with phacoemulsification handpiece 12. The handpiece 12 would additionally provide irrigation fluid 14 via sleeve 15 and irrigation port 17; and aspiration 16 through needle 10*a*, such that irrigation and aspiration may flow to and from the end of handpiece 12 at which the emulsification occurs.

An emulsifying needle 10*a* is associated with horn 10. Disposed about the horn 10 is a plurality of transducers 20. Typically, an oscillating voltage is applied to opposing faces of each of the transducers in order to cause oscillating expansion and contraction of the respective transducers 20. This expansion and contraction causes movement of the horn 10 (in one or more directions, e.g. longitudinal, transversal, torsional, or the like), and thus movement of the emulsifying needle 10*a*, for example, for longitudinal movement, the needle 10*a* moves axially along axis A of FIG. 1.

Figure 2:
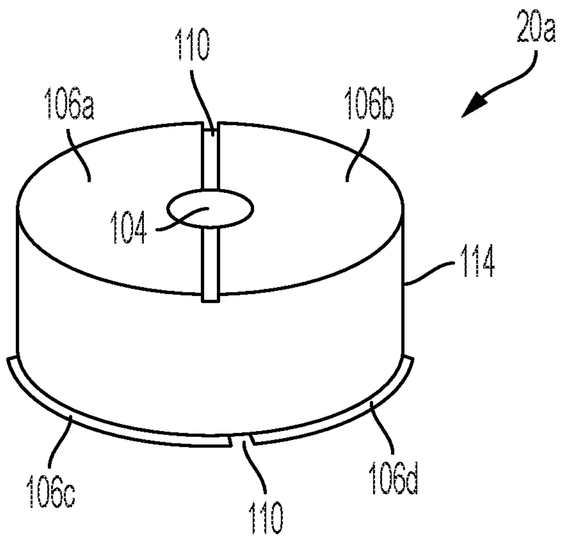
FIG. 2 is an illustration of aspects of the embodiments.

FIG. 2 illustrates a single transducer element 20*a*. The transducer element 20*a* may provide a hole 104 therethrough so as to allow the horn 10, terminating in the needle 10*a*, to pass through the hole 104. The transducer 20*a* may have an at least substantially circular shape.

In the illustrated embodiment, both the top and bottom of the transducer 20*a* include two semi-circular electrodes 106*a, b, c, d*, atop and below halves of a piezoelement, such as a ceramic, 114. The top electrodes 106*a, b*, and the bottom electrodes 106*c, d*, may respectively have therebetween a gap 110. The gap 110 may or may not comprise electrical insulation. Moreover, the gap 110 may additionally extend through the piezoelement 114, such as to add insulating properties in the operations between halves of the transducers 20*a* as discussed throughout.

The electrodes 106*a, b, c*, and *d* may preferably be highly conductive, such as having a metallic composition. By way of non-limiting example, the composition of the electrodes 106*a, b, c*, and *d* may be or include silver. Accordingly, the generation of an electrical potential between the respective left 106*a, c* and right 106*b, d* pairs of the top and bottom electrodes on opposing faces of the piezoelement 114 causes a physical expansion or contraction of the piezoelement 114 portion between the top/bottom pairs of electrodes 106.

Figure 3B:
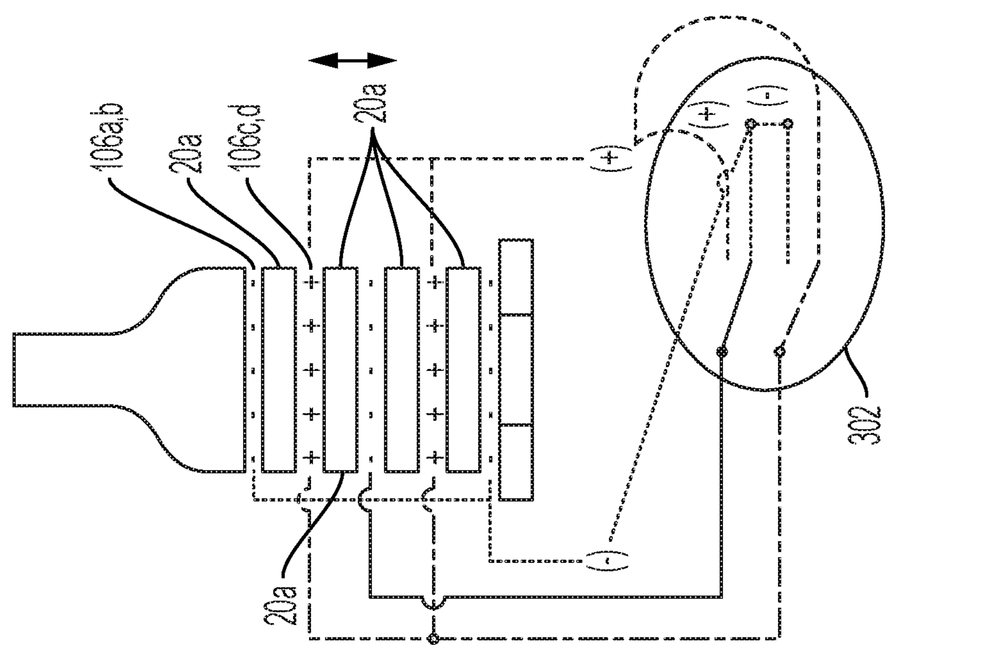
FIGS. 3A and 3B are illustrations of aspects of the embodiments.
Figure 3A:
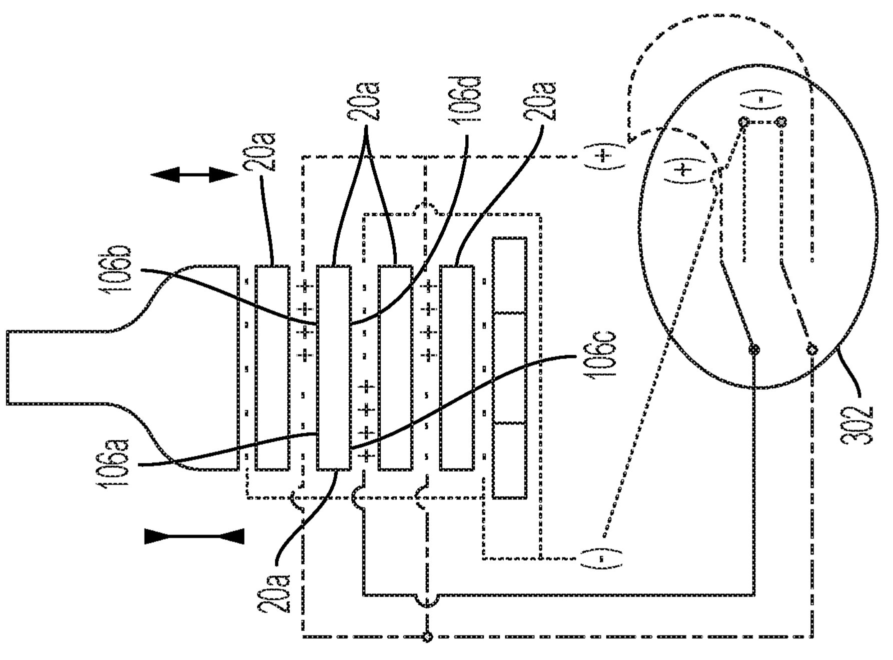

As such, and as illustrated with particularity in FIGS. 3A and 3B, application of a voltage potential in the known manner, such as is illustrated in FIG. 3B, in which alternating opposing potentials are applied to the respective entire "top" (i.e., both top electrodes 106*a, b*), and the respective entire "bottom" (i.e., both bottom electrodes 106*c, d*), of each transducer 20*a*. These applications of voltage, when the DPDT switch 302 is in position 1 as shown in FIG. 3B, effectuate a longitudinal expansion and contraction of each transducer 20*a*, thereby allowing the stack of transducers to drive longitudinal actuation of the correspondent emulsifying needle (not shown in FIG. 3), as will be appreciated by the skilled artisan.

In contrast, when the DPDT switch 302 is in position 2, as shown in FIG. 3A, opposing potentials are not only respectively applied on the top and bottom of each transducer 20*a*, opposing potentials are also applied to each half of the top, and each half of the bottom, of each transducer 20*a*. This corresponds to the application of distinct potentials to each set (i.e., top or bottom) of electrodes 106*a, b* and 106*c, d*, and to each pair (i.e., top left and bottom left, and top right and bottom right) of electrodes 106*a, c* and 106*b, d*. Thereby, each transducer 20*a* will expand on one side thereof, and contract on the other side thereof. As will be appreciated by the skilled artisan, this effectuates a flexural motion in the transducers 20*a*, which causes transversal vibration of the correspondent emulsifying needle (not shown in FIG. 3).

Figure 4B:
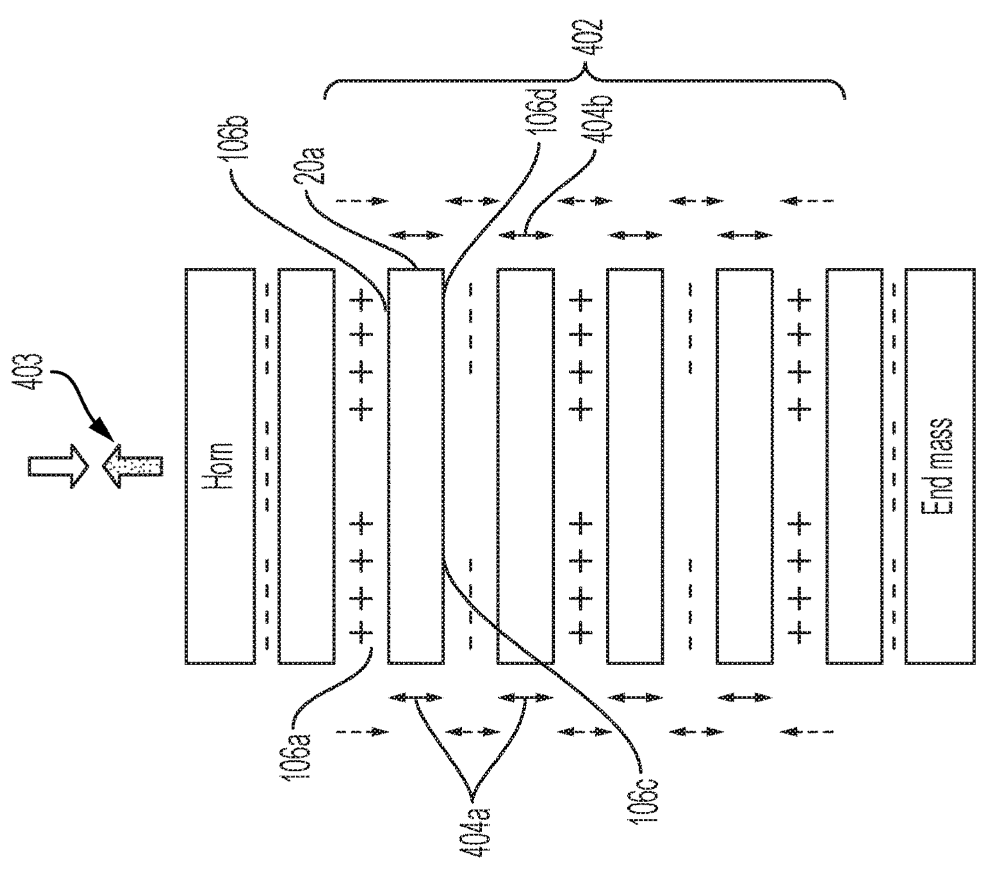
FIGS. 4A and 4B are illustrations of aspects of the embodiments.
Figure 4B:
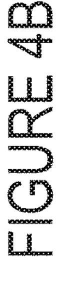
Figure 4A:
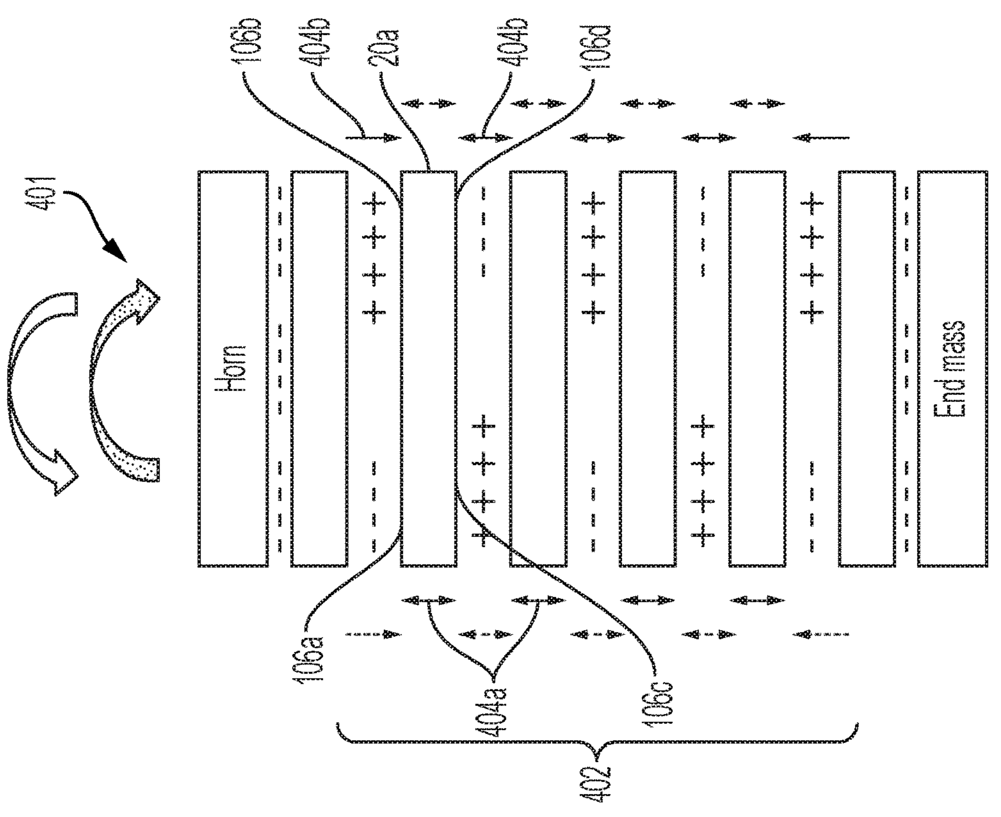

FIGS. 4A and 4B illustrate, with particularity, an exemplary transducer stack 402 in both of the aforementioned modes of operations, and correspondent to position 1 of DPDT 302 (FIG. 3A) and position 2 of same (FIG. 3B). By way of example, FIG. 4A illustrates that the application of opposing potentials to both the sets 106*a, b* and 106*c, d* and pairs 106*a, c* and 106*b, d* of electrodes causes, on each respective transducer 20*a* of the stack 402, opposing behaviors 404*a*, 404*b* on each side of each respective transducer 20*a*. Thereby, the combination of behaviors 404*a*, 404*b* on alternating sides of alternating ones of the transducers 20*a* cause the afore-discussed flexural motion 401 in stack 402.

As was illustrated in FIG. 3B, FIG. 4B shows the operation of stack 402 in longitudinal mode. More particularly, although each pair of electrodes 106*a, c* and 106*b, d* still receives application of opposing potentials, each set of electrodes 106*a, b* and 106*c, d* now has applied thereto the same potential. Accordingly, each side 404*a*, 404*b* of each respective transducer 20*a* in the stack 402 now behaves uniformly with respect to each other side in each electrode set. Thereby, the uniform expansion and contraction of both sides 404*a*, 404*b* of each transducer 20*a* causes the stack 402 to drive a longitudinal motion 403.

Figure 5:
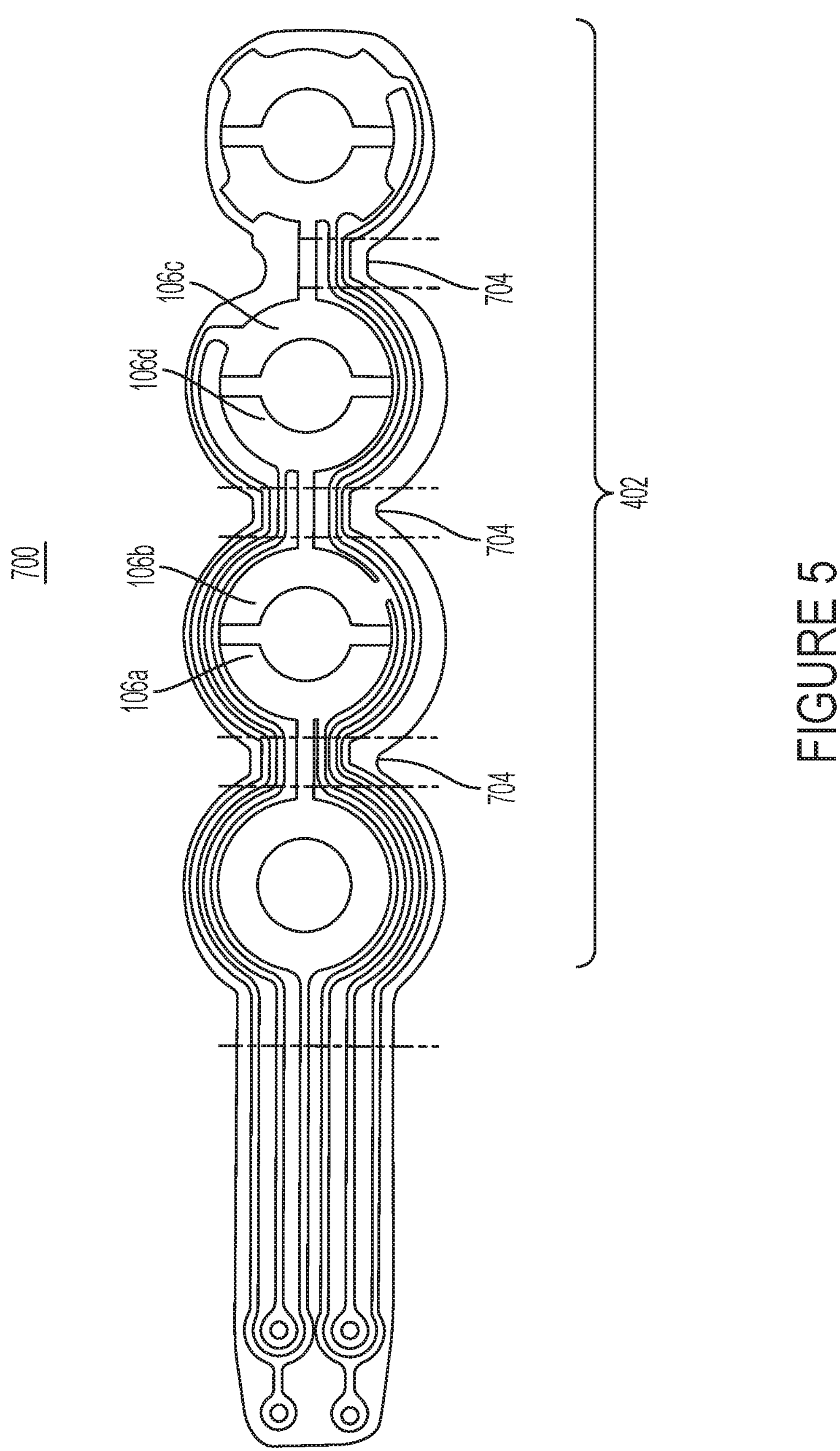
FIG. 5 is an illustration of aspects of the embodiments.

As referenced above, flexible circuits may be formed using additive and/or subtractive printed processes on a flexible substrate. FIG. 5 illustrates an additively manufactured, flexible segmented electrode set system 700 for use in the disclosed embodiments. Of note, although the electrode system 700 illustrated comprises three semicircular sets 106*a, b* and 106*c, d* of electrodes 106 (a+b, c+d) on a flex circuit to perform the function of the electrode sets 106*a, b* and *c, d* discussed above, any number of electrode sets may be used and is dependent upon the number of transducers 20*a* in the stack 402. That is, the provided electrode sets 106*a, b* and *c, d* may engage atop and beneath any number of ones of the plurality of piezoelements 114 in a given transducer stack 402, as discussed herein throughout.

Moreover, the electrical interconnections 704 to the DPDT switch 302 discussed herein, rather than occurring via "hard" interconnections, such as may be used in the foregoing exemplary figures, may be provided via the flexible, additively manufactured electrical interconnections 704 between the electrode sets 106*a, b* and *c, d*, as illustrated in FIG. 5. Also of note with regard to the embodiment illustrated in FIG. 5 and as referenced above, any number of electrode sets 106*a, b* and *c, d* may be provided via the disclosed flexible circuits to the transducer stack 402 in order to obtain the desired longitudinal and transversal performance discussed throughout.

The use of flex circuitry to provide the disclosed segmented electrode sets more readily enables assembly of the disclosed handpiece 12. That is, the nonconductive material on which the additively manufactured flexible circuitry is provided may allow the isolated electrode sets to be held together and flexed about individual transducers 20*a*, thereby aiding in the efficiency and speed of assembly of the transducer stack 402. Further, the providing of isolated interconnecting traces on flex circuits bending around individual transducers 20*a* eliminates the need for the soldering or a like-interconnection of individual wires to each of the segmented electrodes 106*a, b, c, d* in each electrode set from the DPDT switch 302.

Figure 6:
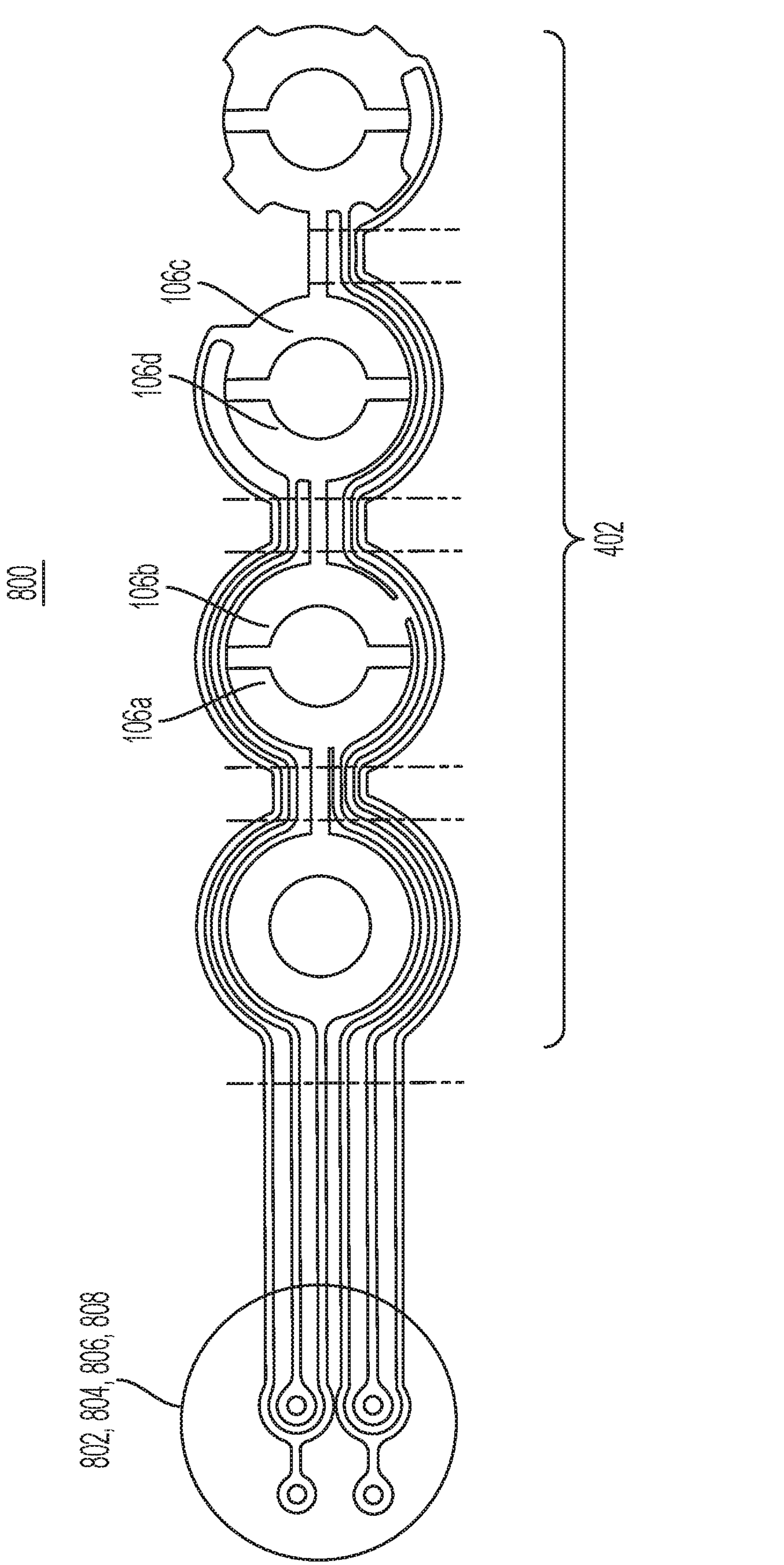
FIG. 6 is an illustration of aspects of the embodiments.

FIG. 6 illustrates a subtractively and/or additively manufactured flex circuit segmented electrode set system 800 for use in the disclosed embodiments. As illustrated in FIG. 6, aspects provided in the embodiment of FIG. 5 may be subtractively removed, such as through known cutting or photolithographic processes, such as in order to decrease the weight and/or increase the flexibility of the segmented electrode sets 106*a, b* and *c, d* provided in the disclosed flex circuit electrode set system 800. That is, by way of comparison between FIGS. 5 and 6, the embodiment of FIG. 6 may eliminate at least ones of those portions of the flex circuit or substrate that do not have additively placed thereon traces to enable into operation of the electrode sets 106*a, b* and *c, d* within the transducer stack 402, as discussed throughout.

Also illustrated in FIG. 6, and provided in a manner similar to that of FIG. 5, are four electrical connections 802, 804, 806, 808 that feed the flex circuit 800, and thereby the electrodes 106*a, b, c*, and *d* within the transducer stack 402. These four interconnections 802, 804, 806, 808 may receive the electrical outputs 624 628, 630 from the DPDT switch 302, as discussed further below.

Figure 7:
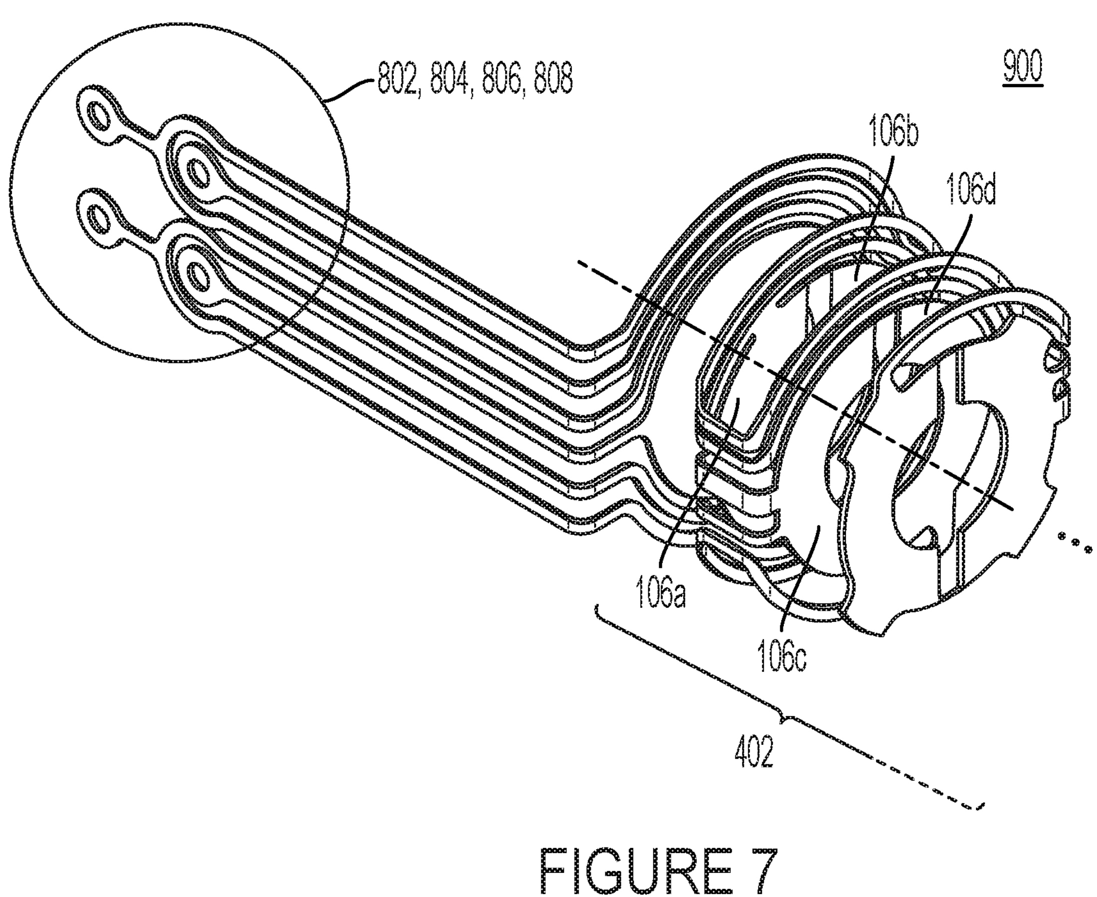
FIG. 7 is an illustration of aspects of the embodiments.

FIG. 7 illustrates the physical arrangement 900 of the flex circuit electrode system 800 provided in the embodiment of FIG. 6, such as to enable placement of the system 800 into the transducer stack 402 of the handpiece 12. For clarity, the piezoelements 114 and/or other aspects of the handpiece 12 and the transducer stack 402 are not shown in the illustration of FIG. 7, to enable a clear illustration of the flexible nature of each interconnect in passing around each piezoelement 114 to provide electrical connections, such as may be dictated by the control system 500 discussed below, to each segmented electrode set 106*a, b, c, d* in the transducer stack 402. Nevertheless, it will be appreciated by the skilled artisan in light of the discussion herein that such other elements, including the piezoelements 114, would be present within the arrangement 900 illustrated in FIG. 7 in operable embodiments. Also of note, evident in FIG. 7 are the four electrical interconnections 802, 804, 806, 808 for receiving outputs of the DPDT switch 302, as discussed above.

Figure 8:
FIG. 8 is an illustration of aspects of the embodiments.
Figure 8:
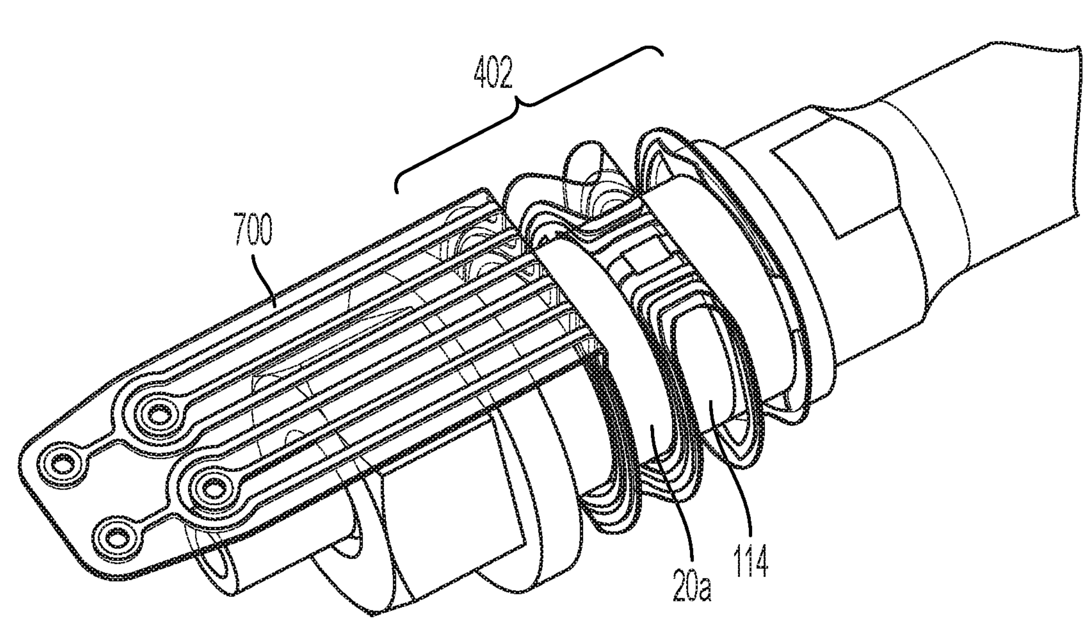

FIG. 8 illustrates the use of the disclosed flex circuit electrode system 700 in a transducer stack 402 of individual transducers 20*a* of a phacoemulsification handpiece Unlike FIG. 7, included in the illustration of FIG. 8 is the plurality of piezoelements 114 in the transducer stack 402 as would be provided in an operable embodiment.

Figure 9:
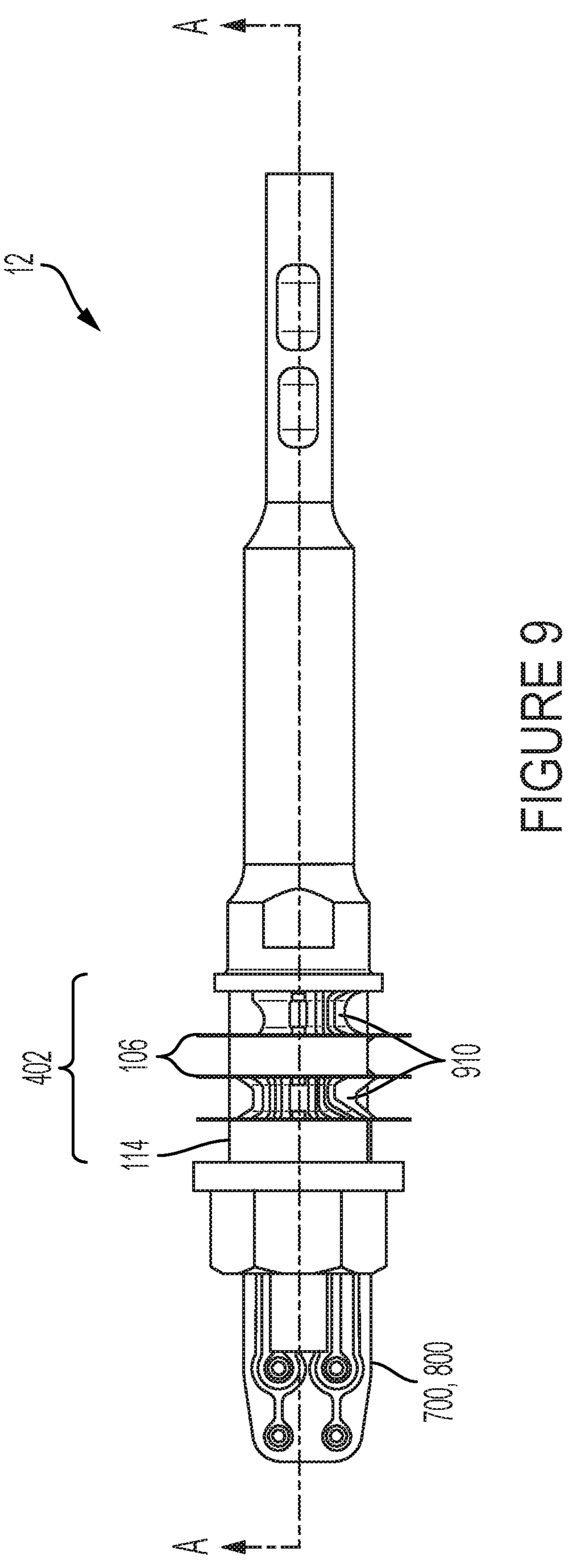
FIG. 9 is an illustration of aspects of the embodiments.

FIG. 9 illustrates a profile view of a internal portion of phacoemulsification handpiece 12 having a transducer stack 402 using the disclosed flex circuit segmented electrode set system 700, 800. As illustrated, some embodiments may include flexible electrical interconnections 910 between electrode sets 106 on alternating sides of the piezoelements 114 as one moves from left to right in the illustration along the transducer stack 402. That is, in an exemplary embodiment, the electrical interconnections 910 may pass around the respective piezoelements 114 in the transducer stack 402 first on one side (e.g. the right side) of the transducer stack 402, then on the other side (e.g. left side), then, for example, on the right side, then on the left side, and so on. It will be appreciated by the skilled artisan that this allows for ease of assembly of handpiece 12 using the flex circuit segmented electrode set system 700, 800, at least in that the flex circuit interconnections 910 may simply be wrapped upon themselves around each electrode set 106*a, b, c, d* and about each piezoelement 114 during the creation of the transducer stack 402 within the handpiece 12.

Figure 10:
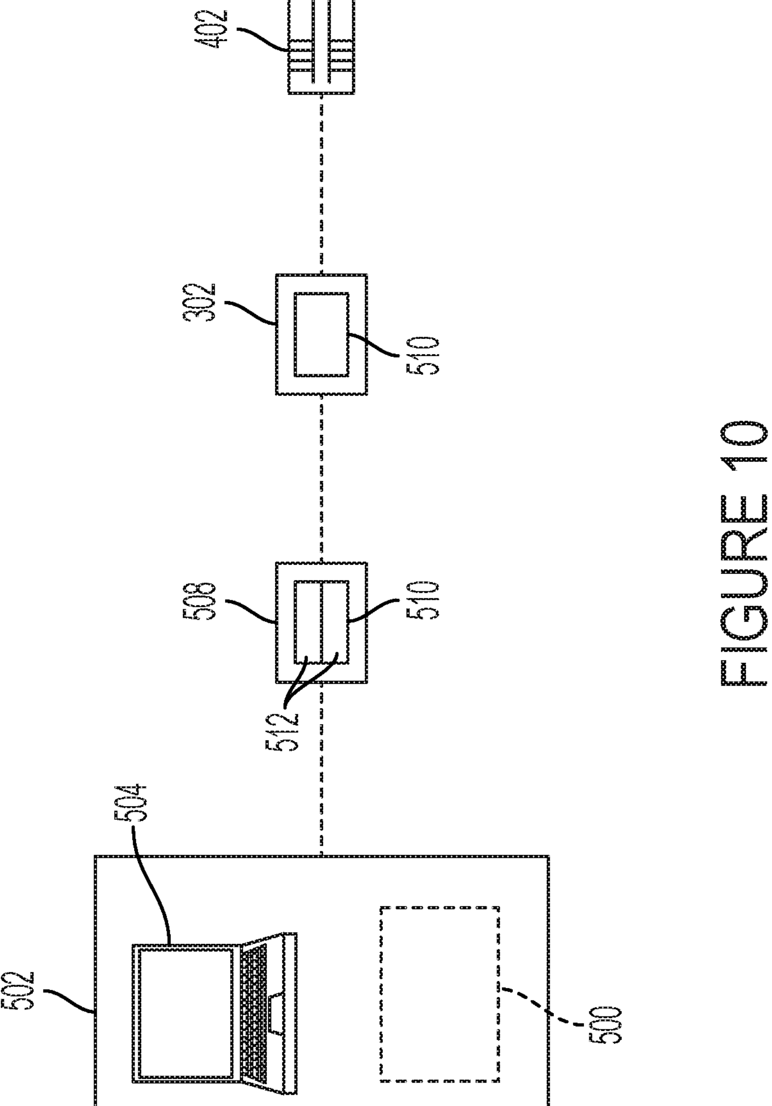
FIG. 10 is an illustration of aspects of the embodiments.

FIG. 10 illustrates the use of a control system 500, such as may reside in a surgical console 502 and be responsive to input to a user interface 504, to control handpiece 12. The control system 500 may be locally or remotely; and wired or wirelessly communicatively associated with user interface 504 and with one or more voltage supplies 508 that are electrically communicative with the DPDT switch 302, and thus with the stack 402 of handpiece 12, as discussed throughout.

The control system 500 may comprise, in part, hardware, software or firmware, or combinations thereof. More specifically, the control system 500 may at least partially comprise non-transitory computing code stored in a computing memory and executed by at least one computing processor.

As referenced above, the DPDT switch 302 may be analog or digital in performance of its disclosed functionality. That is, the DPDT may operate as, in essence, a state machine 510 within the control system 500, whereby the choice of which of the multiple states available to the DPDT switch 302 are controlled by the state machine 510. Of note, and as discussed further herein below, the state machine 510 may also include states for the voltage (such as amplitude and/or frequency) (power source 512) applied to the DPDT switch 302, such as may be based on the choice of state for the DPDT switch 302.

Figures 11A, 11B:
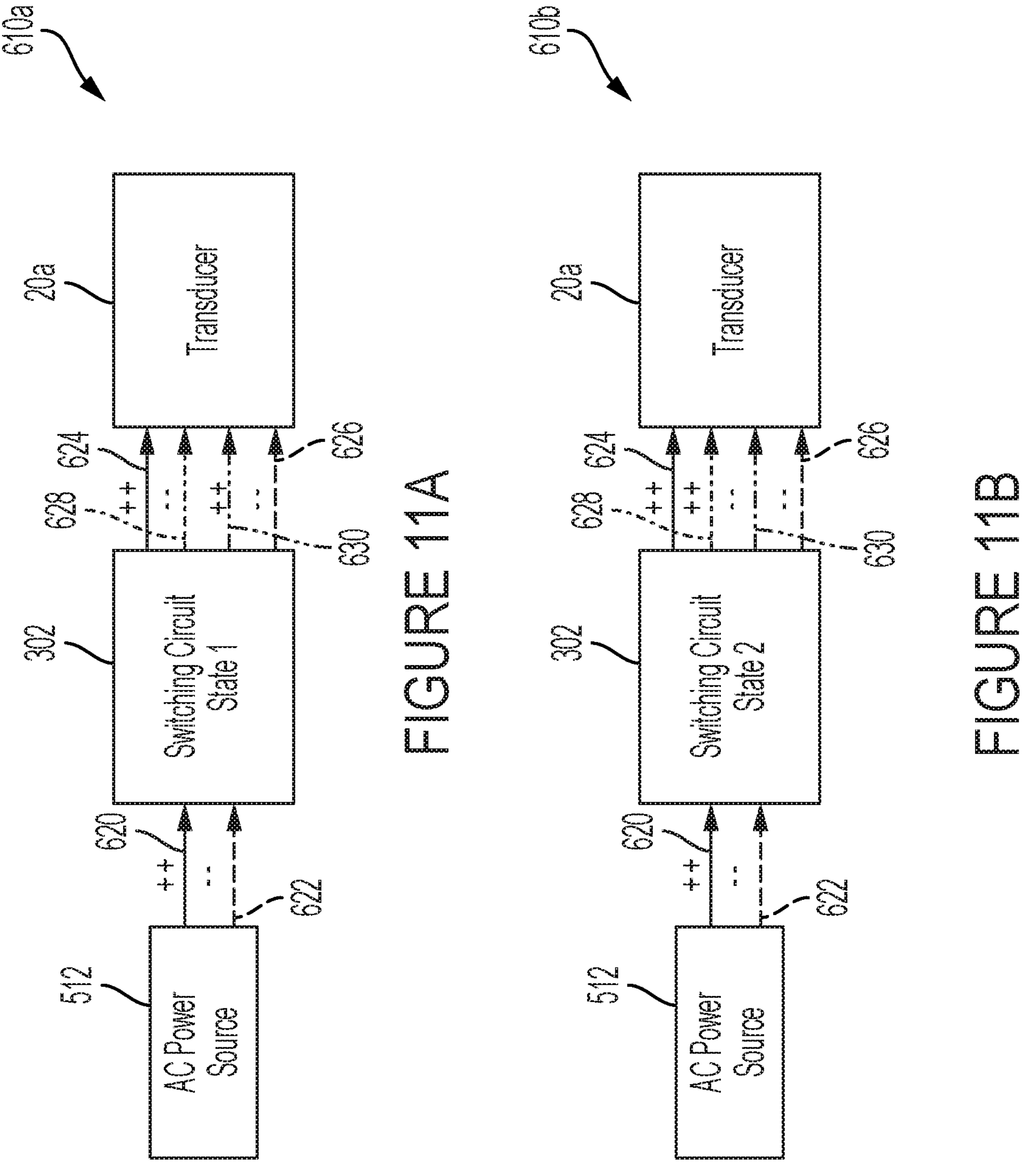
FIGS. 11A and 11B are illustrations of aspects of the embodiments.

By way of non-limiting example, FIGS. 11A and 11B illustrate multiple states 610 for the power source 512 (which, in the illustration, is an AC power source, by way of non-limiting example), the DPDT switch 302, leading to variations in the state of the individual transducers 20*a* and, thereby, the stack 402. Simply put, the resultant states of stack 402 may result in one of the operational states for the handpiece 12 referenced above—that is, for example, either longitudinal and/or transversal vibration of the emulsifying needle associated with handpiece 12.

More specifically, the DPDT switch 302 may receive at least two power leads from power source 512, namely a "positive" lead 620 and a "return" lead 622. The DPDT switch 302 may also provide at least four outputs to each transducer—namely a "positive" output 624, a "return" output 626, an output A 628, and an output B 630.

The state machine 510 may provide at least two states 610 to the DPDT switch 302—namely, "positive" lead 620 to "positive" output 624 and output B 630, and return lead 622 to return output 626 and output A 628; or positive lead 620 to positive output 624 and output A 628, and return lead 622 to return output 626 and output B 630. However, as referenced above, additional states may be provided. By way of example, a third state may provide a power source at a first frequency, such as 30 kHz, by way of non-limiting example; and a fourth state may provide a power source of a second frequency, such as 38.5 kHz. These frequencies may, for example, correspond to the resonance frequencies of the transducer 20*a*.

Control system 500 may control other aspects, in addition to states 610, related to the disclosed embodiments. By way of example, the phases of power provided to the DPDT switch 302 and/or the transducers 20*a*, and the timing of variations thereof, may be controlled by control system 500. Likewise, control system 500 may control, and/or monitor compliance within a predetermined threshold of, various characteristics of the power source 512, which may necessitate actuation of various control circuits, such as feedback control loops (and correspondent sensors), such as may be digital or analog, under the control of control system 500. Such characteristics may include, by way of example, variations in power source output frequency and/or amplitude. By way of example, control system 500 may effectuate a phase shift between electrode sets 106*a, b* and 106*c, d*, thereby causing differing expansions of the right and left side of the piezoelement 114. The aforementioned adjustments available via control system may enable, for example, a real time weighting of longitudinal versus transverse motion during surgery, such as to accommodate surgical needs or preferences.

In the foregoing detailed description, it may be that various features are grouped together in individual embodiments for the purpose of brevity in the disclosure. This method of disclosure is not to be interpreted as reflecting an intention that any subsequently claimed embodiments require more features than are expressly recited.

Further, the descriptions of the disclosure are provided to enable any person skilled in the art to make or use the disclosed embodiments. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but rather is to be accorded the widest scope consistent with the principles and novel features disclosed herein.

What is claimed is:

1. A surgical instrument comprising:

an ultrasonic horn having an emulsifying needle at a distal end thereof;

a plurality of piezoelements about a proximal end of the ultrasonic horn;

a plurality of flexible electrode segments comprising first sets of the electrode segments atop each of the plurality of piezoelements and second sets of the electrode segments below each of the plurality of piezoelements, and comprising at least pairs of the electrode segments in which each pair comprises an electrode segment atop a one of the plurality of piezoelements and a paired electrode segment below that one of the plurality of piezoelements;

a plurality of flexible electrically conductive interconnections that electrically interconnect at least the first sets and second sets, and the pairs, flexibly about each of the plurality of piezoelements; and a power source applied via a controlled double-pole, double-throw (DPDT) switch, wherein a first oscillating uniform excitation of the first sets with a first uniform opposing excitation of the second sets by the power source via the plurality of flexible electrically conductive interconnections effectuates a longitudinal ultrasonic vibration of the ultrasonic horn, wherein a second oscillating uniform excitation of first ones of the pairs with a second uniform opposing excitation of other ones of the pairs via the plurality of flexible interconnections effectuates a transversal ultrasonic vibration of the ultrasonic horn, wherein the plurality of flexible electrode segments and the plurality of flexible electrically conductive interconnections are formed together on a single flexible substrate, wherein each of the piezoelements is cylindrically shaped with a curved lateral surface, and wherein the flexible substrate is arranged on alternating sides of respective curved lateral surfaces of the piezoelements.

2. The surgical instrument of claim 1, wherein the flexible substrate comprises one of poly (ethyleneterephthalate) (PET), poly (ethylene naphthalate) (PEN), poly (imide)-foil (PI), poly carbonate (PC), thermoplastic polyurethane (TPU), paper, textile, PEEK and polyester.

3. The surgical instrument of claim 1, wherein each of the piezoelements provides a hole therethrough to accommodate the ultrasonic horn.

4. The surgical instrument of claim 1, wherein each of the electrode segments is a semi-circle.

5. The surgical instrument of claim 1, wherein each of the piezoelements comprises a ceramic.

6. The surgical instrument of claim 1, wherein each of the electrode segments has a metallic composition.

7. The surgical instrument of claim 6, wherein the metallic composition is beryllium copper.

8. The surgical instrument of claim 1, wherein the first oscillating uniform excitation and the first uniform opposing excitation, or the second oscillating uniform excitation and the second uniform opposing excitation causes one of a physical expansion or contraction of at least a portion of a one of the plurality of piezoelements physically contacted to the excited electrode segments.

9. The surgical instrument of claim 1, wherein the power source comprises two outputs.

10. The surgical instrument of claim 9, wherein the DPDT switch comprises four outputs.

11. The surgical instrument of claim 1, wherein the power source comprises an alternating current voltage source.

12. The surgical instrument of claim 1, wherein the DPDT switch is analog.

13. The surgical instrument of claim 1, wherein the DPDT switch is digital.

14. The surgical instrument of claim 1, further comprising a control system capable of controlling at least the DPDT switch.

15. The surgical instrument of claim 14, wherein the control system is further capable of controlling characteristics of the power source.

16. The surgical instrument of claim 15, wherein the controlled characteristics comprise a phase.

17. The surgical instrument of claim 15, wherein the controlled characteristics comprise a frequency.

* * * * *